United States Patent [19]
Pathak et al.

[11] Patent Number: 6,132,986
[45] Date of Patent: Oct. 17, 2000

[54] TISSUE CROSSLINKING FOR BIOPROSTHESES USING ACTIVATED DIFUNCTIONAL OR POLYFUNCTIONAL ACIDS

[75] Inventors: C. P. Pathak; Mark A. Moore, both of Austin; Richard E. Phillips, San Marcos, all of Tex.

[73] Assignee: Sulzer Carbomedics Inc., Austin, Tex.

[21] Appl. No.: 09/298,211

[22] Filed: Apr. 23, 1999

[51] Int. Cl.[7] .................. G01N 1/30; C12Q 1/02
[52] U.S. Cl. ................. 435/40.5; 435/29; 435/40.52
[58] Field of Search ................. 435/40.5, 29, 40.52

[56] References Cited

U.S. PATENT DOCUMENTS

| | | | |
|---|---|---|---|
| 4,838,888 | 6/1989 | Nashef | 623/2 |
| 5,098,960 | 3/1992 | Frautschi | 525/359.3 |
| 5,147,514 | 9/1992 | Mechanic | 204/157.68 |
| 5,215,541 | 6/1993 | Nashef et al. | 8/94.11 |
| 5,263,992 | 11/1993 | Guire | 623/66 |
| 5,332,475 | 7/1994 | Mechanic | 204/157.68 |
| 5,447,536 | 9/1995 | Girardot et al. | 8/94.11 |
| 5,476,516 | 12/1995 | Seifter et al. | 8/94.11 |
| 5,645,587 | 7/1997 | Chanda et al. | 623/11 |
| 5,697,972 | 12/1997 | Kim et al. | 623/2 |

OTHER PUBLICATIONS

Girardot et al, (Abstract only,) J. of Heart Valve Disease, vol. 5(5), p 518–525, Sep. 1996.

Nielsen, American Journal of Physiology—Cell Physiology, vol. 264/4 33–4 (C823–C835), 1993.

Broom, N.D., "The Stress/Strain and Fatigue Behaviour of Glutaraldehyde Preserved Heart–Valve Tissue", J. Biomechanics, 1997, vol. 10, pp. 707–724.

Gendler, E., "Toxic Reactions Evoked by Glutaraldehyde–Fixed Pericardium and Cardiac Valve Tissue Bioprosthesis", Journal of Biomedical Materials Research, vol. 18, 727–736 (1984).

Girardot, M.N., et al., "Alpha–Aminoleic Acid, a New Compound, prevents Calcification of Bioprostheticheart Valves", The 17th Annual Meeting of the Society for Biomaterials, May 1–5, 1991, p. 114.

Girardot, M.N., et al., "Development of the AOA Process as Antimineralization Treatment for Bioprosthetic Heart Valves", The 19th Annual Meeting of the Society for Biomaterials, Apr. 28–May 2, 1993, p. 266.

Girardot, M.N., et al., "Effect of AOA on Glutaraldehyde–Fixed Bioprosthetic Heart Valve Cusps and Walls: Binding and Calcification Studies", The International Journal of Artificial Organs, vol. 17, No. 2, 1994, pp. 76–82.

Girardot, M.N., et al., "Role of Glutaraldehyde in Calcification of Porcine Heart Valves: Comparing Cusp and Wall", Journal of Biomedical Materials Research, vol. 29, 1995, pp. 793–801.

Golomb, G., et al., "The Role of Glutaraldehyde–Induced Cross–Links in Calcification of Bovine Pericardium Used in Cardiac Valve Bioprostheses", AJP, Apr. 1987, vol. 127, No. 1, pp. 122–130.

Gott, J.P. et al., "Calcification of Porcine Valves: A Successful New Method of Antimineralization", Ann Thorac Surg, 1992, vol. 53, pp. 207–216.

Thubrikar, M.J., et al., "Role of Mechanical Stress in Calcification of Aortic Bioprosthetic Valves", J Thorac Cardiovasc Surg, vol. 86, 1983, pp. 115–125.

Myers, D.J., et al., "Biocompatibility Testing of Stentless Heart Valves Treated with 2–Amino Oleic Acid, a New Antimineralization Agent", The International Journal of Artificial Organs, vol. 16, No. 6, 1993, p. 453.

Munro, M.S., et al., "Alkyl Substituted Polymers with Enhanced Albumin Affinity", Trans Am Soc Artif Intern Organs, 1981, vol. 27, 1981, pp. 499–503.

Moczar, M., et al., "Deterioration of Bioprosthetic Heart Valves", ASAIO Journal 1994, pp. M697–M701.

Magilligan, D.J., "The Future of Bioprosthetic Valves", Trans Am Soc Artif Intern Organs, vol. 34, 1988, pp. 1031–1032.

Levy, R.J., et al., "Bioprosthetic Heart Valve Calcification:Clinical Features, Pathobiology, and Prospects for Prevention", CRC Critical Reviews in Biocompatibility, vol. 2, Issue 2, pp. 147–187.

Thoma, R.J., "Poly (Ether) Urethane Reactivity with Metal–Ion in Calcification and Environmental Stress Cracking", Journal of Biomaterials Applications, vol. 1, Apr. 1987, pp. 449–486.

Goissis, G., et al., "The Chemical Protecting Group Concept Applied in Crosslinking of Natural Tissues with Glutaraldehyde Acetals", Artificial Organs, 22(3), pp. 210–214.

Eberhart, R.C., "Surface Treatments to Improve the Albumin Affinity and Blood Compatibility of Polymers", Engineering in Medicine and Biology Magazine, Jun. 1989, pp. 26–29.

Parnis, S.M., "Acoustic Spectral Analysis of an Electrohydraulic Artificial Heart (TAH)", ASAIO Journal, vol. 41, No. 1, p. 9.

Wiebe, D., "Glutaraldehyde Release from Vascular Prostheses of Biologic Origin", Surgery (104), 1988, pp. 26–33.

Zilla, P., et al., "Improved Ultrastructural Preservation of Bioprosthetic Tissue", J Heart Valve Dis, vol. 6, No. 5, Sep. 1997, pp. 492–501.

(List continued on next page.)

*Primary Examiner*—Louise N. Leary
*Attorney, Agent, or Firm*—Timothy L. Scott; Philip S. Lyren; Kenneth S. Barrow

[57] ABSTRACT

The disclosed invention relates to the process of fixating tissue to obtain tissue for bioprosthetic applications. The fixating process comprises exposing the tissue to a fluid comprising activated difunctional or polyfunctional acids that can react with amino groups in tissue under mild conditions. Activating moieties include disuccinimidyl moieties, n-hydroxy disuccinimidyl moieties, sulfo-disuccinimidyl moieties, and mixtures thereof. The acid is preferably aliphatic difunctional or polyfunctional acids, more preferably a naturally occurring aliphatic difunctional or polyfunctional acids. Even more preferred is an acid consisting of glutaric, suberic acid, sebacic acid, tartaric acid, or mixtures thereof. The activated difunctional or polyfunctional acids are esters comprising the difunctional or polyfunctional acids and the activating moieties.

37 Claims, No Drawings

OTHER PUBLICATIONS

Khor, E., "Methods for the Treatment of Collagenous Tissues for Bioprostheses", Biomaterials, 1997, vol. 18, No. 2, pp. 95–105.

Greene, T. W., et al., "Protection for the CarbonylGroup", Protective Groups in Organic Synthesis, pp. 175–223.

Cheung, D.T., et al., "Mechanism of Crosslinking of Proteins by Glutaraldehyde II. Reaction with Monomeric and Polymeric Collagen", Connective Tissue Research, 1982, vol. 10, pp. 201–216.

Nimni, M.E., "A Defect in the Intramolecular and Intermolecular Cross–Linking of Collagen Caused by Penicillamine", The Journal of Biological Chemistry, vol. 243, No. 7, Apr. 10, 1968, pp. 1458–1466.

Carpentier, A., et al., "Biological Factors Affecting Long–Term Results of Valvular Heterografts", Journal of Thoracic and Cardiovascular Surgery, vol. 58, No. 4, Oct., 1969, pp. 467–483.

Chvapil, M., et al., "Effect of Collagen Crosslinking on the Rate of Resorption of Implanted Collagen Tubing in Rabbits", vol. 11, 1977, pp. 297–314.

Nimni, M.F., et al., "Chemically Modified Collagen: A Natural Biomaterial for Tissue Replacement", Journal of Biomedical Materials Research, vol. 21, 1987, pp. 741–771.

Woodreof, F.A., "Use of Glutara.ldehyde and Formaldehyde to Process Tissue Heart Valves", Processed Tissue Valves, vol. 2, pp. 1–9.

Schoen, F.J., et al., "Cuspal Components in Bioprosthetic Valve Calcification:Elucidation and Modification", Surgery for Heart Valve Disease, 1989, pp. 679–685.

Levy, R.J., et al., "Inhibition by Diphosphonate Compounds of Calcification of Porcine Bioprosthetic Heart Valve Cusps Implanted Subcutaneouslyin Rats", vol. 71, No. 2, Feb. 1985, pp. 349–356.

Webb, C.L., et al., "Al+++ Preincubation Inhibits Calcification of Bioprosthetic Heart Valve Tissue in the Rat Subdermal Model", Trans Am Soc Artif Intern Organs, vol. 34, 1988, pp. 855–859.

Baldwin, M., et al., "Fe3+ Pretreatment Provides Sustained Inhibition of Bioprosthetic Heart Valve Calcification", The 17th Annual Meeting of the Society for Biomaterials, May 1–5, 1991, p. 61.

Bernacca, G.M., et al., "Chemical Modification of Bovine Pericardium and its Effect on Calcification in the Rat Subdermal Model", Biomaterials, 1992, vol. 13, No. 6.

Chanda, J., "Prevention of Calcification of Heart Valve Bioprostheses:An Experimental Study in Rat", Ann Thorac Surg, 1995, 60, S339–S342.

Vesely, I., et al., "The Hybrid Xenograft/Autograft Bioprosthetic Heart Valve: In Vivo Evaluation of Tissue Extraction", Ann Thorac Surg, 1995, 60, S359–S364.

Okoshi, T., et al., "A New Bioprosthetic Cardiac Valve with Reduced Calcification", ASAIO Transactions 1990, 36, pp. M411–M414.

Moore, M.A., et al., "Stabilization of Pericardial Tissue by Dye–Mediated Photooxidation", Journal of Biomedical Materials Research, vol. 28, 1994, pp. 611–618.

Oster, G., et al., "Dye Sensitized Photooxidation", J. Am. Chem. Soc. Oct. 5, 1959, vol. 81, pp. 5095–5099.

Cao, H., et al., "Characterization of Mechanical Properties of Photooxidation Modified Bovine Pericardium", 21st Annual Meeting of the Society for Biomaterials, Mar. 18–22, 1995, p. 82.

TISSUE CROSSLINKING FOR BIOPROSTHESES USING ACTIVATED DIFUNCTIONAL OR POLYFUNCTIONAL ACIDS

FIELD OF THE INVENTION

The present invention relates to a method of preparing tissue for prosthetic use that has excellent mechanical properties and that does not prevent the attachment and spreading of host cells, i.e., endothelial cells, on the bioprosthesis necessary for long term biocompatibility. The method comprises fixating the tissue with an activated difunctional or polyfunctional acid, such as disuccinimidyl glutarate or bis(sulfosuccinimidyl) suberate.

BACKGROUND OF THE INVENTION

Tissue transplantation is a rapidly growing therapeutic field as a result of improvements in surgical procedures, immuno-suppressive treatments, and increased knowledge of the graft-host interaction. Despite major advances, problems associated with tissue transplantation include inflammation, degradation, calcification, and rejection of the transplanted tissue.

There are several applications for tissue transplantation. Heart malfunction due to heart valve disorders can often be treated by surgically implanting a prosthetic valve. Treated tissue derived from porcine aortic valves or bovine pericardium, is currently used in prosthetic heart valves. Tissue must be stabilized prior to implantation into an animal different from the donor animal. This process of stabilization is known in the art as fixation. The fixation process makes the tissue more resistant to degradation upon implantation. It also makes it non immunogenic so that it will not be rejected by the host human body.

Generally, the fixation process operates by blocking reactive molecules on the surface of and within the donor tissue, thereby rendering it substantially non-antigenic and suitable for implantation as well as crosslinking the collagenous matrix providing stability. Collagenous tissue, usually the major component of a typical bioprosthesis, can be fixated by a number of methods, including treating the material with aldehydes. Glutaraldehyde is the most common reagent used in the fixation of animal tissue. Glutaraldehyde is easily available, bifunctional, inexpensive and reacts under physiological conditions with primary amine groups of collagen molecule. However, there are some significant problems with glutaraldehyde fixation method. The Schiff-base bond between collagen and glutaraldehyde is unstable in nature. Glutaraldehyde polymerizes in water to produce a water soluble polyether polymer. The glutaraldehyde treated tissue is more susceptible to calcification. Glutaraldehyde is cytotoxic. Finally, the polymeric product of glutaraldehyde produces glutaraldehyde by depolymerization reaction of its polymeric form, the polyether. The leaching of cytotoxic glutaraldehyde is believed to prevent cellular growth on the bioprosthesis necessary for long term biocompatibility.

The problems associated with the glutaraldehyde fixed tissue led to the development of alternative tissue fixatives. The state of the art of tissue fixation is well documented in the literature (recent review article by Eugene Khor, Tissues, Volume 18, page 95–105 and reference therein). Other bifunctional or polyfunctional tissue reactive reagents known in the art include polyepoxides, diisocyanates, polyfunctional acids, a di-functional acid, and 1,6-hexane diamine, carbodiimides and photooxidation using organic dyes. These treatments have varying success in replacing glutaraldehyde as a tissue crosslinking agent, but none of these has achieved the success of the glutaraldehyde fixation.

Efforts at retarding the calcification of bioprosthetic tissue have been numerous in recent years. The techniques resulting from these efforts may be broadly divided into two categories; those involving the pre- or post-treatment of glutaraldehyde-fixed tissue with one or more compounds that inhibit calcification (or modify the fixed tissue to be less prone to calcification) and those involving the fixation of the tissue with compounds other than glutaraldehyde, thereby reducing calcification.

The former category of techniques includes, but is not limited to, treatment with such compounds as:

a) detergent or surfactant, after glutaraldehyde fixation;

b) diphosphonates, covalently bound to the glutaraldehyde-fixed tissue or administered via injection to the recipient of the bioprosthesis or site-specifically delivered via an osmotic pump or controlled-release matrix;

c) amino-substituted aliphatic functional acid, covalently bound after glutaraldehyde-fixation;

d) sulfated polysaccharides, especially chondroitin sulfate, after glutaraldehyde fixation and preferably followed by treatment with other matrix-stabilizing materials;

e) ferric or stannic salts, either before or after glutaraldehyde fixation;

f) polymers, especially elastomeric polymers, incorporated into the glutaraldehyde-fixed tissue; or g) water-soluble solutions of a phosphate ester or a quaternary ammonium salt or a sulfated higher aliphatic alcohol, after glutaraldehyde-fixation.

The latter category of techniques for reducing the calcification or bioprosthetic tissue, i.e., techniques involving the fixation of the tissue with compounds other than glutaraldehyde, includes but is not limited to, the following:

a) treatment by soaking the bioprostetic tissue in an aqueous solution of high osmolality containing a photo-oxidative catalyst and then exposing said tissue to light thereby fixing the tissue via-photo-oxidization; and b) fixation via treatment with a polyepoxy compound, such as polyglycidyl ether (polyepoxy) compound.

A recently reported fixation method uses a coupler and a coupling enhancer with or without one or more coupling agents. It fixes the tissue by linking the amine and the carboxyl moieties through amide bonds either directly, or indirectly when coupling agents form bridges. Tissue is fixed using the coupling agents such as 1,6-hexane diamine and suberic acid in the presence of the coupler such as 1-ethyl-3(3-dimethyl aminopropyl) carbodiimide hydrochloride and a coupling enhancer N-hydroxysulfosuccinimide.

In most cases, investigations related to glutaraldehyde-associated sympotomatology have been limited to specific problems such as calcification and have not addressed the entire spectrum of symptoms. Thus, while the problem of calcification of glutaraldehyde-fixed bioprostheses has received a great deal of attention, the proposed solutions have generally failed to address any other complications presented by the presence of glutaraldehyde, such as toxicity, immune reactions and degeneration. Glutaraldehyde released from the tissue is cytotoxic and prevents the formation of endothelial cell growth on the bioprosthesis necessary for long-term durability. This persistent damage to the implant and surrounding tissue due to the long-term slow release of glutaraldehyde may be fully eradicated only by using a fixation process that does not include glutaraldehyde. The complexity and gravity of the clinical problems resulting from glutaraldehyde-preserved bioprostheses warrant the search for an alternative fixation method.

What is needed in the art is a fixation method that can 1) be performed quickly and if necessary in vitro, 2) does not introduce cytotoxic chemicals or other material that will hinder the adhesion and growth of host endothelial cells, 3) that provides adequate fixation under conditions of normal pH, and 4) does not promote calcification.

SUMMARY OF THE INVENTION

This invention relates to a process of fixating tissue to obtain tissue for bioprosthetic applications. The fixating process comprises exposing the tissue to a fluid comprising activated polyfunctional acids that can react with amino groups in tissue under mild conditions. The activated polyfunctional acids of this invention comprise two or more functional acid moieties (i.e. polyfunctional) and one or more activating moieties. Activating moieties include disuccinimidyl moieties, n-hydroxy disuccinimidyl moieties, sulfo-disuccinimidyl moieties, and mixtures thereof. The acid moiety is preferably aliphatic polyfunctional acids, more preferably a naturally occurring aliphatic polyfunctional acids. Even more preferred is an acid moiety of glutaric, suberic acid, sebacic acid, tartaric acid, or mixtures thereof. The activated polyfunctional acids are esters comprising the difunctional or polyfunctional acid moieties and the activating moieties.

DETAILED DESCRIPTION OF THE INVENTION

This invention is a process of fixating tissue to obtain tissue for bioprosthetic applications. The invention is also the tissue fixed by said process.

As used herein, the term "bioprosthesis" is meant to include any prosthesis which is derived in whole or part from animal or other organic tissue and which is to be implanted in a mammal. Thus, the term generally includes prostheses such as heart valves and other heart components, vascular replacements or grafts, heart replacements, urinary tract and bladder replacements, bowel and tissue resections in general and the like. As a general rule, the particular tissue utilized as the starting material is determined by the intended use of the product. For instance, if it is desired to build a heart valve from the product of the process of the present invention, the preferred starting tissue is a tissue having a high collagen content such as the pericardium, for instance, bovine pericardium. If the cross-linked product is to be used as a vascular graft, such starting materials as the aortic arch of rats or other relatively small animals or the carotid artery of pigs, sheep, or cows are used to advantage. To make injectable collagen, finely ground reconstituted bovine skin collagen is used. If the use will be for artery replacement, urinary tract and bladder replacements, orthopedic applications such as bone or cartilage repair bowel and tissue resections in general and the like, the biotissue selected will often have the same function in the donor animal. The choice will depend on the desired properties that the prosthesis should have.

As used herein the term "tissue" is meant to include any material which is derived in whole or part from animal or other organic tissue, and which is to be implanted in a mammal. The tissue often comprises one or more of collagen, collagen fibrils, and collagen matrices. The fixation using the process of this invention is not limited to one tissue type such as collagen-rich bovine pericardium. Other types of tissues which can contain different types of proteins such as elastin can also be crosslinked using the process of this invention.

The term "crosslink" is defined as understood by those of skill in the art. Generally, where biological tissue is concerned, cross-linking refers to the process of forming covalent bonds (or cross-links) either directly between free active moieties on or within the tissue or between the free active moieties of the tissue and one or more compounds (or cross-linking agents), in such a manner as to leave few or no active moieties on or within the tissue. This cross-linking process "fixes" or stabilizes the tissue by making the tissue less antigenic and thus less susceptible to degradation than before the process.

Thus the term "fixation" as used herein, and as generally understood by those of skill in the art, refers to the process of treating biological tissue in order to stabilize it for implantation in a host animal different from the donor individual. "Fixating" and "crosslinking" are used interchangeably herein. Currently, most bioprosthetic tissue is fixed via treatment with glutaraldehyde.

A "crosslinking agent", as used herein, is a compound capable of binding to the free active moieties of prosthetic tissue and/or to other cross-linking agents in such a manner as to result in cross-linking between and within the molecules of the prosthetic tissue and between the molecules of the prosthetic tissue and the agent, thereby fixing said tissue. The cross-linking agent(s) is selected in such a way as to maximize fixation of the tissue being treated while minimizing the risk of damage to the prosthesis during treatment and minimizing the risks, such as of toxicity, inflammation, calcification, etc. to the host animal in whom the treated prosthesis is to be implanted. The cross-linking agents are preferably water-soluble so that aqueous buffers may be utilized thereby minimizing the risk of damage to the prosthesis during the fixation process.

The fixating process comprises exposing the tissue to a fluid comprising activated difunctional or polyfunctional acids that can react with amino groups in tissue under mild conditions.

"Exposing" means soaking the tissue in a fluid comprising the fixating agent for a period of time sufficient to fixate the tissue. The soaking is often by immersion, swirling, or vortexing. While some agitation will reduce the amount of time needed, the mechanics of exposing the tissue to the fluid are not important.

As used herein, the term "fluid" includes solutions, suspensions, emulsions and gels. The fluid contains sufficient quantities and concentrations of the crosslinking agent to allow crosslinking of tissue when the tissue is exposed to the fluid for a sufficient period of time.

As used herein, the term "activated" as applied to difunctional and polyfunctional acids means an acid moiety-containing compound containing an additional moiety such that the activated acid can react with amino groups under mild conditions. Preferred activating moieties include disuccinimidyl moieties, n-hydroxy disuccinimidyl moieties, sulfo-disuccinimidyl moieties, and mixtures thereof. The more preferred activating moiety are those that form a molecule that has sufficient solubility in water to not require additional surfactants. The most preferred activating moiety is a sulfo-disuccinimidyl moiety. Said moieties are attached to said acids in any manner, however, the preferred embodiment of the crosslinking agent is an ester comprising the difunctional or polyfunctional acid moeities and the activating moieties. The n-hydroxysuccinimide or sulfohydroxysuccinimide ester of glutaric, suberic acid, sebacic acid, or tartaric acid are examples of compounds that can be used in the process of the present invention.

The tissue is exposed to a fluid comprising activated polyfunctional acids. As used herein polyfunctional acid includes difunctional acid, unless specified otherwise. While the acid moiety can be any acid difunctional or polyfunctional acid moiety, it is preferred that the acid moiety be a naturally occurring aliphatic difunctional or polyfunctional acid moiety. By naturally occurring it is meant that the acids exist in some quantity in the host mammal, or are metabolizable by the host mammal. The acids may under some conditions be partially metabolized, and naturally occurring aliphatic difunctional or polyfunctional acids will have less danger of being metabolized into a cytotoxic compound, even with the activating moiety attached. The fixated tissue, also does not leach cytotoxic compounds that prevent cellular growth on the bioprosthesis that is necessary for long term biocompatibility. Preferred acid moieties are glutaric acid, suberic acid, sebacic acid, tartaric acid, or mixtures thereof. The most preferred acid moiety is suberic acid. Other diacids: sccinic acid, itnionic acid, adipic acid, pimelic acid, azelaic acid, sebacic acid, dodecandioc acid, 1-12-dodecanedicarboxylic acid, hexadecanedioic acid.

Disuccinimidyl glutarate, for example, is a derivative of glutaric acid which is capable of crosslinking tissues. Disuccinimidyl glutarate is an example of a water insoluble, homo or bifunctional n-hydroxysuccinimide ester reagent which can react with proteins. The insolubility in water can inhibit exposure of the tissue to the disuccinimidyl glutarate.

A preferred n-hydroxysuccinimide ester is one that is water soluble, such as sulfonated n-hydroxysuccinimide ester as crosslinking agent for tissues. The substitution of the $SO_3$ groups on the N-hydroxysuccinimide ring improves water solubility and maintains reactivity with primary amine. The compound disulfosuccinimidyl suberate is an example of a water soluble crosslinking agent. A crosslinking agent with two activating moieties, i.e., bis (sulfosuccinimidyl) suberate, is the most preferred embodiment of an activated difunctional acid of this invention.

The term "water soluble", as used herein, denotes a substance with sufficient solubility that an aqueous fluid contains sufficient quantities and concentrations of the substance to allow crosslinking of tissue when the tissue is exposed to the fluid. The term "solubility-enhancing compound" is meant to include any compound or material that increases the capacity of a fluid to carry an increased quantity of compounds that are useful in the process of this invention. Surfactants and emulsifiers, for example dimethylsulfoxide, are examples of solubility-enhancing compounds.

An embodiment of the present invention is to use a solubility-enhancing compound in addition to the insoluble, the slightly soluble, and even for the soluble n-hydroxysuccinimide esters of the present invention. For example, crosslinking of bovine pericardium using sparingly soluble disuccinimidyl glutarate was carried out with 10% dimethylsulfoxide in water. The addition of dimethylsulfoxide helps to solubilize the disuccinimidyl glutarate into the aqueous medium. Dimethylsulfoxide may also act as tissue penetration enhancer for disuccinimidyl glutarate. The quantity of the solubility-enhancing material should be at least enough so that the quantity of the crosslinking agent carried by the fluid is sufficient to crosslink the tissue.

Because the crosslinking agents used during the fixation process of the present inventory and their by-products are water-soluble, or at least soluble in an aqueous solution comprising solubility enhancing compounds, the excess crosslinking agents are easily removed by washing.

Primary amines in the tissue are a target of both glutaraldehyde fixation and fixation by the process of the current invention. The fixating process forms bonds between amines, making the tissue more inert and more biocompatible in a different host. The amide bonds thus formed are believed to be more stable than the Schiff-base bonds formed by glutaraldehyde.

The fixating process comprises exposing the tissue to a fluid comprising activated difunctional or polyfunctional acids that can react with amino groups in tissue under mild conditions. The term "mild conditions" means fluid conditions such that the proteins are not changed or denatured. The fluid medium is, therefore, preferably water. The fluid is preferably a buffered saline solution. The pH can range from about pH 6 to about pH 10, preferably from about pH 6.5 to about pH 8, more preferably from about pH 6.8 to about pH 7.5, most preferably from about pH 7.1 to about pH 7.4. By saline, the solution can be any solution normally used in tissue fixation. Preferred are saline phosphate buffer solution (phosphate buffer solution) and high saline high sugar solutions. The temperature can range from about 0° C. to about 60° C., preferably from about 2° C. to about 30° C., more preferably from about 4° C. to about 21° C.

It is sometimes advantageous to expose the tissue to the fluid comprising the crosslinking agent for a period of time at ambient temperature, and then for a longer period of time at refrigerator conditions of about 4° C. Very long periods of tissue storage in a fixating solution may not provide any additional benefit. The minimum time for exposure of tissue to fluid comprising the crosslinking fluid is about 5 minutes, preferably about 15 minutes, more preferably 30 minutes, and most preferably about 6 hours. The maximum amount of time the tissue may be exposed to the fluid comprising the crosslinking agent is generally not important. Exposure for about 48 hours may be appropriate under some conditions, though generally exposure for less than about 24 hours is needed, and often exposure for less than about 12 hours is needed to fixate the tissue.

The process of this invention may be used in combination with other fixation technologies, preferably a second process that also does not cause the fixated tissue to leach cytotoxic compounds, to provide a range of tissue properties. For example, it may be advantageous to fix tissue with both the process of photooxidation and with the process of this invention. For example, photo-oxidized bovine pericardium tissue was advantageously crosslinked using disuccinimidyl glutarate. Photooxidation process and materials described in U.S. Pat. No. 5,332,475 to Mechanic, and U.S. Pat. No. 5,147,514 to Mechanic are incorporated here by reference. Additional refinements as described by Moore, et al., J. Biomed. Matl. Res., 28:611–18, 1994 are also compatible with the present invention. The n-hydroxysuccinimide esters can enhance the tissue properties, for example, by increasing the shrink temperature and modules, of photo-oxidized tissue. The process of this invention can be used in combination with other fixating techniques, such as those techniques presented in the background section.

Another embodiment of this invention utilizes an n-hydroxysuccinimide ester in a non-aqueous medium, for example in an alcohol, to carry out the crosslinking reaction. The reaction of disuccinimidyl glutarate with primary amine groups results in the release of N-hydroxysuccinimide. The hydrolysis reaction n-hydroxysuccinimide ester with water is a major competing reaction of n-hydroxysuccinimide-acylation reaction. However, the use of an n-hydroxysuccinimide ester in isopropanol is not preferred. Without being bound to any theory, it is believed that the primary amines in the tissue, which is the target for crosslinking, may be unavailable due to denaturing in an isopropanol environment. In some cases it may be advantageous to us a medium like isopropanol where the crosslinking agent specifically reacts with contaminants such as bacteria and acts as a sterilant.

The crosslinking reaction is fast relative to other crosslinking techniques and can be carried out in aqueous medium under very mild conditions such as physiological conditions, i.e., in a saline solution at pH 7.2. Crosslinking of tissue with several disuccinimidyl and sulfo-disuccinimidyl esters of di-acids was observed at pH of 7 and pH of 9. The temperature of the fixation is not important. Because the fixation is rapid and can be performed in solutions similar to physiological conditions, this fixation process may be particularly preferred for 'in situ' fixation of tissues during a surgical procedure. The speed of this reaction can be further enhanced by optimizing reaction variable like concentration, temperature and pressure.

Another preferred embodiment of this invention comprises terminating the unreacted n-hydroxysuccinimide esters on the tissue with biologically active compounds like heparin. This can be achieved by crosslinking the tissue with n-hydroxysuccinimide ester first and then subsequently reacting with a heparin solution.

The invention also relates to the tissue produced by this process. The tissue that was crosslinked by the process of this invention supports cellular growth while glutaraldehyde crosslinked tissue does not support cellular growth. The term "supports cellular growth" means that under certain conditions certain cells can adhere and survive on the tissue. In particular, tissue fixated by the process of this invention can under appropriate circumstances have endothelial cells adhere and grow thereon. Without being bound to any theory, it is believed that the tissue fixated by the process of this invention does not leach cytotoxic compounds which inhibit cell viability and growth. Endothelial cells do not attach and spread on glutaraldehyde fixed tissue.

EXAMPLES

The following examples are included to demonstrate embodiments of the invention. However, those of skill in the art should, in light of the present disclosure, appreciate that many changes can be made in the specific embodiments which are disclosed and still obtain a like or similar result without departing from the spirit and scope of the invention.

Fresh and photooxidized bovine pericardium stored in high-salt high-sugar (HSHS) solutions were used in all examples described herein. Bovine and porcine tissues were collected from slaughter house within 30 minutes after the kill. Usually, within 36 hours, the tissues were cleaned to remove excess fat, connective tissue, rinsed with cold phosphate buffered saline and stored in hyperosmotic storage solution (HSHS solution) until fixation. Bis (sulfosuccinimidyl) suberate (DSS) and disuccinimidyl glutarate (DSG) were purchased from Pierce (Rockford, Ill.). All the other chemicals such as glutaraldehyde, sodium chloride were reagent grade and were obtained from standard laboratory chemicals suppliers such as Sigma, Aldrich etc. Bovine pericardium tissue was cut into 1 cm diameter circles using a Ingersoll R waterjet cutting machine (Model 25S). The cell culture experiments were performed using a standard cell/tissue culture laboratory capable of handling and growing mammalian and human cell cultures.

Examples 1–9

Samples of bovine pericardium were crosslinked using bis(sulfosuccinimidyl) suberate. Two pieces of bovine pericardium tissue (size 0.2×0.2 cm. approximate weight 12 mg per piece) were suspended in a 1 ml plastic centrifuge tube containing 0.2 ml of aqueous phosphate buffered (pH=7.2) saline fluid. A total of 0.005 g of bis(sulfosuccinimidyl) suberate was added to the fluid. The mixture was vortexed for 5 minutes. The crosslinking reaction was continued for 6 hours at room temperature. Some samples were then washed with 50% ethanol several times and stored in refrigerator. Other samples stayed in the fixating solution another 12 hours at about 4° C. before being washed with 50% ethanol several times and stored in the refrigerator.

Samples of bovine pericardium were crosslinked using disuccinimidyl glutarate using the same procedure as described above, except that a total of 0.04 grams of dimethylsulfoxide and 0.005 g disuccinimidyl glutarate were added to the fluid in place of the bis(sulfosuccinimidyl) suberate.

Control samples include unfixated tissue, tissue that has undergone photooxidation fixation using methylene blue and visible light irradiation, and tissue that has undergone standard glutaraldehyde fixation using a 2.5% glutaraldehyde in a phosphate buffer solution.

The fixation technique for each sample are presented in Table 1.

TABLE 1

Bovine Pericardium Tissue Crosslinking Reaction Conditions

| Example | Reaction medium/pH | Cross-linker | Time/Temp |
|---|---|---|---|
| 1 | No treatment | None | None |
| 2 | Photooxidized | None | None |
| 3 | 2.5% GA in phosphate buffer solution at pH 7.2 | GA | 6 h at room temp and 12 h at 4° C. |
| 4 | Photooxidized, then PBS with 20% DMSO at pH 7.2 | DSG | 6 h at room temp and 12 h at 4° C. |
| 5 | PBS with 20% DMSO at pH 7.2 | DSG | 6 h at room temp and 12 h at 4° C. |
| 6 | Sodium borate at pH 9.0 | DSG | 6 h at room temp and 12 h at 4° C. |
| 7 | Isopropanol | DSG | 6 h at room temp and 12 h at 4° C. |
| 8 | Phosphate buffer solution at pH 7.2 | DSG | 6 h at room temp |
| 9 | Sodium borate at pH 9.0 | DSS | 6 h at room temp |

Where GA is glutaraldehyde, DMSO is dimethylsulfoxide, DSG is disuccinimidyl glutarate, and DSS is bis (sulfosuccinimidyl) suberate.

The effectiveness of a fixation process is related to a value called the shrinkage temperature. The shrinkage temperature was determined using standard differential scanning calorimetric analysis. Briefly, 2–10 mg of tissue are heated at about 10° C. per minute under nitrogen atmosphere. The endotherm that occurs at around 60–80° C. is typically referred as shrinkage temperature. The onset temperature is used as shrinkage temperature.

Shrink temperature and polyacrylamide gel electrophoretic analysis of tissue extracts were performed to confirm the crosslinking of bovine pericardium using n-hydroxysuccinimide esters. The results of both the tests are summarized in Table 2. The control or untreated sample had a shrinkage temperature of 64.4° C. This is a typical value for untreated bovine pericardium tissue. The photo-oxidized control tissue had a shrinkage temperature 64.0° C. When disuccinimidyl glutarate is reacted with tissue in aqueous medium, the shrinkage temperature increased above 70° C. indicating crosslinking of tissues. The pH of the medium had little effect on shrinkage temperature. However, when the reaction was carried out in non aqueous medium such as isopropanol, the shrinkage temperature (63.8° C.) did not change as compared to untreated tissue, indicating very little crosslinking. This may be attributed to the unavailability of primary amines groups in non aqueous medium. In many instances, the shrinkage temperature of n-hydroxysuccinimide crosslinked tissue is close to 74° C. This value is similar to glutaraldehyde crosslinked tissue (75–80° C.).

TABLE 2

Shrinkage Temperature and Extractable Proteins Analysis

| Example | Treatment | Shrinkage Temp. (° C.) | Extractable Proteins |
|---|---|---|---|
| 1 | No treatment | 64.4 | Present |
| 2 | Standard Photooxidized | 64.0 | Absent |
| 3 | Glutaraldehyde treated | 82.2 | Absent |
| 5 | DSG treated, pH 7 | 74.3 | Absent |
| 4 | Standard Photooxidized and DSG treated, pH 7 | 74.9 | Absent |
| 6 | DSG treated, pH 9 | 71.0 | Absent |
| 7 | DSG treated in isopropanol | 63.8 | Present |
| 8 | DSS treated pH 7 | 73.3 | Absent |
| 9 | DSS treated pH 9 | 71.5 | Absent |

Evidence of crosslinking is also given by a protein extraction assay. Crosslinking results in less extractable protein from tissue. Protein extraction assays have the following general procedure: 10–20 mg of tissue was extracted with 10–20 microliter extraction solution containing 50 mM Tris-HCl (pH 6.8), 10% glycerol, 4% mercapto ethanol, 1% sodium dodecyl sulfate, 0.5M NaCl, and 0.01% bromophenol blue. The extracted solution was then analyzed on a 4–20% acrylaminde:bisacrylamide (37.5:1 Mini-PROTEAN II ready Gel (Biorad, Richmond, Calif.).

The results support the conclusions reached on examination of the shrinkage temperature. The n-hydroxysuccinimide ester treatment in aqueous medium and glutaraldehyde treatment showed substantial reduction in extractable proteins indicating crosslinking of the tissue. The n-hydroxysuccinimide acylation reaction in isopropanol showed substantial extractable proteins confirming no crosslinking.

Adhesion and spreading of bovine endothelial cells in Dubelco's Modification of Eagals Medium supplemented with 10% fetal calf serum was used to test of the effect of crosslinking method on endothelial cell adherence and growth. A standard tissue laboratory protocol was used to culture endothelial cells. The cells were seeded at a known density on crosslinked tissues and the cells were grown for 2 days using standard tissue culture laboratory protocol. At the end of 48 h period, the endothelial cells were fixed using 4% formaldehyde and stained using phalloidan stain. The cells were then visualized using fluorescence microscopy. The results of endothelial cell adhesion and growth are recorded in Table 3.

TABLE 3

Adhesion and Spreading of Bovine Endothelial Cells on Crosslinked Tissue

| Example | Treatment | Cell Attached | Cells Spread |
|---|---|---|---|
| 1 | No treatment | Yes, on all surface | Yes, on all surface |
| 2 | Standard Photooxidized | Yes, on all surface | Yes, on all surface |
| 3 | Glutaraldehyde treated | Only isolated spots | No |
| 4 | Photooxidized and DSG treated, pH 7 | Yes, on all surface | Yes, on all surface |
| 8 | DSS treated pH 7 | Yes, on all surface. | Yes, on all surface |

The endothelial cells did not attach and spread on glutaraldehyde fixed tissue. This may be attributed to the leaching of cytotoxic glutaraldehyde by the glutaraldehyde fixed tissue. All the other tissue samples showed normal attachment and spreading of endothelial cells on the tissue. This indicates that the crosslinked tissue obtained using n-hydroxysuccinimide esters support cellular growth.

Examples 10–17

The following set of examples were performed to determine the kinetics of fixation using DSS is bis (sulfosuccinimidyl) suberate. Eight circular pieces of bovine pericardium, stored in HSHS solution, were rinsed with phosphate buffer solution and then soaked in 30 ml of phosphate buffer solution for 30 minutes. The pieces were then transferred into 50 ml sterile plastic centrifuge tube containing 20 ml of phosphate buffer solution. Then, 100 mg of bis(sulfosuccinimidyl) suberate powder was directly added to the centrifuge tube. After vortexing for 15 minutes, one circular piece was removed from the fixation solution, washed with phosphate buffer solution and stored in 20 ml 50% ethanol. Similarly, other pieces were taken out at 0.5 h, 1 h, 2 h, 3 h, 6 h and 12 h time interval, rinsed with phosphate buffer solution, and stored in 50% ethanol. These pieces were then subjected to shrink temperature and extraction analysis. Untreated tissue was used as control.

The results are given in Table 3. Most of the crosslinking is achieved within first 15 minutes, and there is little apparent improvement after 30 minutes. This indicates that the crosslinking reaction is faster as compared to other crosslinking agents such epoxy based crosslinking agents reported in the literature. For example, Z. Tang et al. Reported that the ethane diglycidyl ether and other epoxy based crosslinking agents took about 20–100 hours to achieve complete crosslinking based on crosslinking reaction time/shrinkage temperature study.

TABLE 3

Shrinkage Temp. and Fixation Time, 5 g/L bis(sulfosuccinimidyl) suberate

| Example | Hours | Shrinkage Temperature (° C.) |
|---|---|---|
| 10 | 0 | 63.6 |
| 11 | 0.25 | 71.5 |
| 12 | .5 | 73.6 |
| 13 | 1 | 73.4 |
| 14 | 2 | 72.9 |
| 15 | 3 | 72.8 |

TABLE 3-continued

Shrinkage Temp. and Fixation Time, 5 g/L bis(sulfosuccinimidyl) suberate

| Example | Hours | Shrinkage Temperature (° C.) |
|---|---|---|
| 16 | 6 | 71.9 |
| 17 | 12 | 73.6 |

Examples 18–25

In these examples different types of tissue were crosslinked. The tissue types bovine pericardium, bovine thoracic artery, porcine heart valve cusp, and porcine heart wall. The procedure used was identical for each tissue type. The degree of crosslinking was then tested by determining the shrinkage temperature. An untreated tissue sample was used for comparison. The fixation procedure for porcine aortic root is given below.

The tissue, i.e., a one third section of porcine aortic root containing one cusp and one attachment zone, was transferred to 50 ml sterile plastic centrifuge tube containing 10 ml phosphate buffer solution. A total of 100 mg of bis(sulfosuccinimidyl) suberate reagent was directly added to the tube and the solution was vortexed for 15 minutes. The fixation reaction continued for an additional six hours with gentle shaking and was terminated by washing 3 times with 20 ml phosphate buffer solution. Finally, the tissue was stored in 30 ml 50% ethanol.

Table 4 presents the results of the shrinkage temperature test performed on tissues fixed using bis(sulfosuccinimidyl) suberate. The fixation using bis(sulfosuccinimidyl) suberate is not limited to one tissue type such as bovine pericardium. Other types of tissues which can contain different types of proteins such as elastin can also be crosslinked using bis(sulfosuccinimidyl) suberate. Porcine heart wall, porcine heart valve cusp, bovine thoracic artery, and bovine pericardium all showed an increase in shrink temperature as compared to corresponding untreated or uncrosslinked tissue, indicating crosslinking. The treated tissue also showed reduced or no extractable protein as compared to untreated or control tissue, again confirming the crosslinking of tissue.

TABLE 4

Tissues Fixed With Bis(sulfosuccinimidyl) Suberate

| Example | Type of Tissue Fixed | Shrink Temperature (° C.) |
|---|---|---|
| 18 | Treated porcine heart wall | 73.4 |
| 19 | Untreated porcine heart wall | 64.2 |
| 20 | Treated porcine heart valve cusp | 77.6 |
| 21 | Untreated porcine heart valve cusp | 64.9 |
| 22 | Treated bovine thoracic artery | 74.6 |
| 23 | Untreated bovine thoracic artery | 63.7 |
| 24 | Treated bovine pericardium | 73.3 |
| 25 | Untreated bovine pericardium | 64.4 |

Example 26

In this example the degree of penetration of the crosslinking agent was determined. A one third section of porcine aortic root containing one cusp and one attachment zone was transferred to 50 ml sterile plastic centrifuge tube containing 10 ml phosphate buffer solution. A total of 100 mg of bis(sulfosuccinimidyl) suberate reagent was directly added to the tube and the solution was vortexed for 15 minutes. The fixation reaction continued for an additional six hours with gentle shaking and was terminated by washing 3 times with 20 ml phosphate buffer solution. Finally, the tissue was stored in 30 ml 50% ethanol.

The porcine wall near the non coronary cusp was about 3–4 mm thick. A 3 mm×3 mm piece of the tissue was removed from wall and dissected using surgical scalpel along the thickness of the wall. The tissue was sectioned into 4 pieces. The first and fourth section represented the tissue along the surface, in direct contact with the fixating solution, whereas second and third section represented the tissue inside the thick wall. All the four sections were subjected to shrink temperature analysis. The results are presented in Table 5.

TABLE 5

Shrink Temperature of Sectioned Porcine Aortic Root

| Tissue Section | Shrink Temperature (° C.) |
|---|---|
| Section 1 | 74.4 |
| Section 2 | 71.8 |
| Section 3 | 71.8 |
| Section 4 | 72.6 |
| Untreated control | 64.2 |

The sections 2 and 3 (the inner tissue) have slightly lower shrinkage temperatures as compared to section 1 and 4 (tissue on the surface). All the sections, however, have higher shrink temperatures compared uncrosslinked control sample. These results indicate that the bis(sulfosuccinimidyl) suberate was able to penetrate the tissue and to crosslink thick tissue essentially uniformly under our crosslinking conditions.

Example 27–31

This set of examples tested the ability under appropriate circumstances to have endothelial cells adhere and grow on tissue fixated by the process of this invention.

Bovine pericardium tissue samples fixed using crosslinking agents including bis(sulfosuccinimidyl) suberate, glutaraldehyde, and photooxidized tissue (using methylene blue and visible light irradiation) were used in this set of examples. In addition, bovine pericardium tissue sample fixed first by photooxidation with methylene blue/visible light and later with disuccinimidyl glutarate was also used in this experiment. The fixation followed the procedures given for Examples 1 to 10. Untreated bovine pericardium tissue was used as control.

For each example, a one centimeter square tissue sample was soaked in 70% ethanol overnight, and then washed with sterile phosphate buffer solution three times over 15 minutes. The tissue sample was then soaked in Minimum Essential Medium (a cell growth substrate) supplemented with aminoacids, antibiotics and 30% fetal bovine serum for ninety minutes. The tissue samples were then transferred to a sterile tissue culture plate. Bovine aortic endothelial cells suspended in a 90% Minimum Essential Medium /10% fetal bovine serum were placed on the tissue samples at approximately 200,000 cells per tissue. The cells were allowed to adhere for 30 minutes before adding 0.75 ml of the same medium to each sample. After 24 hours of incubation in a 95% air/5% carbon dioxide atmosphere at 98% humidity and 37° C., the samples were transferred to new sterile tissue culture plates and fresh medium was added to these plates. The samples were incubated for a further period of 24 hours.

At the end of this incubation period, the tissue samples/cells were washed three times with phosphate buffer solution over 15 minutes at room temperature. The tissue and cells were then treated with 4% paraformaldehyde for 10 minutes. After rinsing the samples in phosphate buffer solution as described above, they were treated with 0.1% Triton X100 in phosphate buffer solution for 3 minutes. The cells were then stained with phalloidin/rhodamine (diluted 1:40 in phosphate buffer solution) in dark for 45 minutes, rinsed 3 times in phosphate buffer solution, and viewed immediately under a fluorescence microscope. The morphology and coverage of endothelial cells on tissue samples are presented in Table 7.

TABLE 7

Adhesion and Spreading of Bovine Endothelial Cells on Crosslinked Tissue

| Example | Treatment | Area Covered by Cells | Cells Morphology |
|---|---|---|---|
| 27 | No treatment | >70% | Cells attached and spread with normal spindle shape morphology |
| 28 | Photooxidized | >70% | Cells attached and spread with normal spindle shape morphology |
| 29 | Glutaraldehyde | <10% | Cells not attached or spread |
| 30 | Photooxidized, and DSG treated, pH 7 | >70% | Cells attached and spread with normal spindle shape morphology |
| 31 | DSS treated, pH 7 | >70% | Cells attached and spread with normal spindle shape morphology. |

The uncrosslinked bovine pericardium and bis (sulfosuccinimidyl) suberate, photooxidized tissue, and photooxidized/disuccinimidyl glutarate fixed tissue crosslinked supported the attachment and growth of bovine arotic endothelial cells. This indicate the crosslinked tissue is not leaching any cytotoxic chemicals which will inhibit the attachment and growth of these cells in the tissue culture medium. On the other hand glutaraldehyde fixed tissue showed little or no attachment of endothelial cells. Without meaning to be bound by any theory, the lack of attachment and growth on this example was thought to be the result of leaching of cytoxic glutaraldehyde. It is known that glutaraldehyde is cytotoxic at 3 ppm in tissue culture medium. The leaching of glutaraldehyde from GA fixed tissue is thought to be associated with the depolymerization of its polymeric product and/or reversibility of crosslinking reaction.

Examples 32–35

Bovine pericardium tissue crosslinked using bis (sulfosuccinimidyl) suberate, disuccinimidyl glutarate and glutaraldehyde were subcutaneously implanted. The glutaraldehyde fixed samples were provided by Labcor (Brazil). The bis(sulfosuccinimidyl) suberate and disuccinimidyl glutarate fixed samples were stored in 50% ethanol whereas glutaraldehyde fixed sample was stored in glutaraldehyde solution. One $cm^2$ diameter disks were implanted using a standard surgical protocol. Prior to implantation, the tissues were rinsed for 3 minutes in each of three basins containing 500 ml of sterile phosphate buffer solution, accompanied by gentle shaking. Specimens were implanted subcutaneously 1 cm lateral from the abdominal midline in 3 week old Sprague-Dawley rats and retrieved after 90 days. Unimplanted samples, and implanted but uncrosslinked samples, were used as controls.

At explant, after visual analysis, the samples were sectioned, stained with H&E and Masson's trichrome then evaluated histologically for biocompatibility. Biocompatibility includes an evaluation of inflammation, vascularization, and collagen organization. Inflammation consists of aggregates of lymphocytes and plasma cells, and the presence of mast cells in the implants. Vascularization indicated the presence of capillaries or other blood vessels infiltrating the implant. Masson's trichrome stain distinguishes the host fibrous response from the fibrous tissue of the implant. It determines changes in collagen bundles, such as dense collagen without normal banding or increased fibrillar appearance. Van Kossa indicated the calcification of tissue by staining calcium phosphate in the tissue. Biocompatibility, an average of the above described tests, was reported on a scale of 0 to 5, 0 being best. The overall results showed bis(sulfosuccinimidyl) suberate fixed samples (Example 32) and glutaraldehyde fixed samples (Example 33) had average scores of 2.0. The samples fixed with disuccinimidyl glutarate (Example 34) had an average score of 3.0, and the uncrosslinked samples (Example 35) had an average score of 3.8.

The uncrosslinked BP showed a reduction in size indicating partial degradation and resorption of the implant. The three crosslinked samples did not show visual change in size or appearance of degradation indicating resistance to degradation. The histology of the explants showed low inflammatory response to all crosslinked tissue.

Fixed tissue, especially glutaraldehyde-fixed tissue, has an undesirable tendency to calcify. The calcium content of the implants was determined by the wet-ashing technique. About 0.5 g of explanted tissues were weighed and wet-ashed by heating up to 250° C. with 4 ml of concentrated sulfuric acid followed by heating to 300° C. with addition of concentrated nitric acid. The resulting digested samples were brought to 40 ml with addition of high purity water. Calcium concentration was determined by standard ICP methodology. The data for calcium analysis of explanted tissue samples are shown Table 7.

TABLE 7

Calcium Content of Tissue Explanted After 90 Days Subcutaneous Implantation

| Tissue Treatment | Valid # | Calcium, Mean ± S.D. (mg/g tissue) |
|---|---|---|
| Disuccinimidyl glutarate Implanted | 8 | 21.2 ± 39.7 |
| Bis(sulfosuccinimidyl) suberate Implanted | 8 | 0.2 ± 0.0 |
| Glutaraldehyde Implanted | 4 | 76.9 ± 11.0 |
| Uncrosslinked Implanted | 6 | 2.1 ± 4.3 |
| DSG Unimplanted | 2 | 0.1 ± 0.0 |
| DSS Unimplanted | 2 | 0.1 ± 0.1 |
| GA Unimplanted | 2 | 0.3 ± 0.2 |
| Uncrosslinked Unimplanted | 2 | 0.1 ± 0.0 |

The glutaraldehyde fixed implanted tissue showed statistically significant (p<0.05) higher levels of calcium as compared to other implanted tissue. The bis (sulfosuccinimidyl) suberate fixed samples showed less tendency to calcify as compared to samples fixed with disuccinimidyl glutarate.

Example 36

Samples of bovine pericardium tissue crosslinked in accordance with the present invention as described in examples 1–9, as well as several controls were subjected to pepsin and cyanogen bromide digestion assay. The aqueous reactions were carried out at pH 7 and 9 with 10% dimethylsulfoxide (DMSO) as organic solvent. The addition of dimethylsulfoxide helps to solubilize the disuccinimidyl glutarate into the aqueous medium. Dimethylsulfoxide may also act as tissue penetration enhancer for disuccinimidyl glutarate.

Bovine pericardium tissue fixed using bis (sulfosuccinimidyl) suberate or disuccinimidyl glutarate was subjected to pepsin digestion. Uncrosslinked tissue sample was used as control. Tissue samples were clipped into small fragments and digested for 4 h at 37° C. in 10 mM HCl solution containing 4 mg/ml pepsin. The enzyme:tissue ratio was 1:2500 (weight:weight). Sham digestions were also prepared in HCl without the enzyme. Following incubation, the samples were centrifuged at 4° C. for 1 hour at 14,000 rpm. The supernatants were stored at 4° C. overnight. Prior to gel electrophoresis, 100μ of supernatant was lyophilized and prepared with sample buffer. A 10–20% acrylamide:bisacrylamide (37.5:1) gradient gel was loaded. Control samples with the same quantity of enzyme were also incubated as above, but in the absence of tissue.

Crosslinked bovine pericardium tissue as well as uncrosslinked tissue were treated with cyanogen bromide (CNBr) and analyzed by polyacrylamide gel electrophoresis. Two 10±1 mg, sample fragments were prepared from each of the pericardium samples. One set of sample fragments, was incubated at 55° C. overnight in a buffered beta mercaptoethanol solutions, the other set of fragments was incubated overnight at 4° C. in fifty percent ethanol. After the incubation both sets of sample fragments were rinsed well with water and transferred to fresh microcentrifuge tubes. The CNBr Digestion occurred at 30° C. for 4 hours with 1 ml of a 50 mg/ml CNBr solution in 70% formic acid. One tenth of the reaction volume was removed, diluted 10-fold with water, lyophilized and prepared for electrophoresis. The sample aliquots were run on a 10–20% acrylamide:bisacrylamide (37.5:1) gradient gel.

Pepsin digested fraction of uncrosslinked tissue showed substantial proteins indicating poor resistance to pepsin digestion. In bis(sulfosuccinimidyl) suberate and disuccunimidyl glutarate crosslinked tissue, no protein fraction in sham as well as pepsin digested reactions were seen, indicating significant resistance to pepsin induced degradation. Glutaraldehyde crosslinked tissue also showed resistance to pepsin digestion. The porcine heart wall and cusp crosslinked by bis(sulfsuccinimidyl) and analyzed by pepsin digestions assay showed similar resistance to digestion. The results of CNBr digestion assay showed the presence of large amounts of extractable proteins for uncrosslinked tissue where as bis(sulfosuccinimidyl) suberate, disuccinimidyl glutarate and glutaraldehyde crosslinked showed little or no extractable proteins indicating resistance or CNBr digestion.

What is claimed is:

1. A process of fixating tissue, said method comprising exposing the tissue to fluid comprising activated polyfunctional acids, said acids comprised of a polyfunctional acid moiety and an activating moiety, for a time sufficient for crosslinking to occur.

2. The process of claim 1 wherein the activated polyfunctional acids are esters.

3. The process of claim 1 wherein the polyfunctional acid moiety is an aliphatic acid moiety.

4. The process of claim 1 wherein the polyfunctional acid moiety is a naturally occurring aliphatic acid moiety.

5. The process of claim 1 wherein the polyfunctional acid moiety comprises a glutaric acid moiety, a suberic acid moiety, a sebacic acid moiety, adipic acid moiety, pimelic acid, dodecandoic acid, 12-dodecanedicarboxylic acid, hexadecanedioic acid or mixtures thereof.

6. The process of claim 1 wherein the polyfunctional acid moiety is a suberic acid moiety.

7. The process of claim 1 wherein the activating moiety is a disuccinimidyl moiety, a n-hydroxy disuccinimidyl moiety, or a sulfo-disuccinimidyl moiety.

8. The process of claim 1 wherein the activating moiety is a sulfo-disuccinimidyl moiety.

9. The process of claim 1 wherein the activated polyfunctional acid is a n-hydroxysuccinimide ester of glutaric acid, suberic acid, sebacic acid, or tartaric acid; a sulfohydroxysuccinimide ester of glutaric acid, suberic acid, sebacic acid, or tartaric acid; or mixtures thereof.

10. The method of claim 1 wherein the activated polyfunctional acid is a sulfo-hydroxysuccinimide ester of glutaric acid, suberic acid, sebacic acid, or tartaric acid, or mixtures thereof.

11. The method of claim 1 wherein the activated polyfunctional acid comprises a sulfo-hydroxysuccinimide ester of suberic acid.

12. The method of claim 1 wherein the activated polyfunctional acid comprises bis(sulfosuccinimidyl) suberate.

13. The method of claim 1 wherein the activated polyfunctional acid comprises disulfosuccinimidyl suberate.

14. The method of claim 1 wherein the fluid further comprises a solubility-enhancing compound.

15. The method of claim 14 wherein the solubility-enhancing compound comprises dimethylsulfoxide.

16. The method of claim 14 wherein the activated polyfunctional acid comprises disuccinimidyl glutarate.

17. The method of claim 1 wherein the fluid is an aqueous buffer solution with a pH from about pH 6 to about pH 10.

18. The method of claim 1 wherein the fluid is an aqueous buffer solution with a pH from about pH 6.5 to about pH 8.

19. The method of claim 1 wherein the fluid is an aqueous buffer solution with a pH from about pH 6.8 to about pH 7.5.

20. The method of claim 1 wherein the fluid is an aqueous buffer solution with a pH from about pH 7.1 to about pH 7.3.

21. The method of claim 1 wherein the fluid is at a temperature from about 0° C. to about 60° C.

22. The method of claim 1 wherein the fluid is at a temperature from about 2° C. to about 30° C.

23. The method of claim 1 wherein the tissue is exposed to the fluid for at least about 15 minutes.

24. The method of claim 1 wherein the tissue is exposed to the fluid for at least about 30 minutes.

25. The method of claim 1 wherein the tissue is exposed to the fluid for at least about 6 hours.

26. The method of claim 1 further comprising fixating the tissue with other fixation technologies that do not cause the fixated tissue to leach cytotoxic compounds.

27. The method of claim 26 further comprising fixating the tissue with photooxidation.

28. The method of claim 1 further comprising subsequently exposing the fixated tissue to a biologically active compound that terminates the unreacted activating moieties on the tissue.

29. The method of claim 1 further comprising subsequently exposing the fixated tissue to a fluid comprising heparin.

30. The method of claim 1 wherein at least some exposure of tissue to the fluid comprising activated polyfunctional acids occurs 'in situ' during a surgical procedure.

31. Fixated tissue, wherein the tissue is fixated by a process comprising exposing the tissue to a fluid comprising activated polyfunctional acids, said activated polyfunctional acids comprising a polyfunctional acid moiety and an activating moiety, for a time sufficient for crosslinking to occur.

32. The tissue of claim 31 wherein the activated polyfunctional acid is a n-hydroxysuccinimide ester of glutaric acid, suberic acid, sebacic acid, or tartaric acid; a sulfohydroxysuccinimide ester of glutaric acid, suberic acid, sebacic acid, sccinic acid, adipic acid, primelic acid, azelaic acid, dodecandioc acid, 1,12-dodecanedicarboxylic acid, hexadecanedioic acid or mixtures thereof.

33. The tissue of claim 31 wherein the activated polyfunctional acid comprises bis(sulfosuccinimidyl) suberate.

34. The tissue of claim 31 wherein the tissue is also fixated with other fixation technologies that do not cause the fixated tissue to leach cytotoxic compounds.

35. The tissue of claim 34 wherein the other fixation technology is photooxidation.

36. The tissue of claim 34 wherein the tissue after fixation was subsequently exposed to a biologically active compound that terminates the unreacted activating moieties on the tissue.

37. The tissue of claim 31 wherein the tissue does not leach cytotoxic compounds which inhibit cell viability and growth.

* * * * *